United States Patent
Munsinger et al.

(10) Patent No.: US 9,662,235 B2
(45) Date of Patent: May 30, 2017

(54) HANDLE FOR DELIVERING MEDICAL DEVICE

(71) Applicant: Boston Scientific Scimed, Inc., Maple Grove, MN (US)

(72) Inventors: Joel R. Munsinger, Blaine, MN (US); Gary J. Pederson, Jr., Albertville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 438 days.

(21) Appl. No.: 13/855,301

(22) Filed: Apr. 2, 2013

(65) Prior Publication Data

US 2013/0268049 A1 Oct. 10, 2013

Related U.S. Application Data

(60) Provisional application No. 61/620,172, filed on Apr. 4, 2012.

(51) Int. Cl.
*A61F 2/95* (2013.01)
*A61F 2/966* (2013.01)

(52) U.S. Cl.
CPC ............... *A61F 2/95* (2013.01); *A61F 2/966* (2013.01); *A61F 2002/9517* (2013.01); *F04C 2270/0421* (2013.01)

(58) Field of Classification Search
CPC .... A61F 2/95; A61F 2/82; A61F 2/966; A61F 2/954; A61F 2002/9517; A61F 2002/9665; A61F 2002/011
See application file for complete search history.

(56) References Cited

U.S. PATENT DOCUMENTS

| | | | |
|---|---|---|---|
| 5,897,564 A * | 4/1999 | Schulze et al. | 606/148 |
| 6,599,296 B1 | 7/2003 | Gillick et al. | |
| 7,122,050 B2 | 10/2006 | Randall et al. | |
| 7,674,282 B2 | 3/2010 | Wu et al. | |
| 2002/0072753 A1* | 6/2002 | Cohen | 606/103 |
| 2003/0191516 A1 | 10/2003 | Weldon et al. | |
| 2004/0006380 A1* | 1/2004 | Buck et al. | 623/1.11 |
| 2004/0186511 A1 | 9/2004 | Stephens et al. | |
| 2005/0080476 A1 | 4/2005 | Gunderson et al. | |
| 2005/0149159 A1 | 7/2005 | Andreas et al. | |
| 2005/0256562 A1 | 11/2005 | Clerc et al. | |
| 2009/0099641 A1 | 4/2009 | Wu et al. | |
| 2009/0118740 A1 | 5/2009 | Mangiardi et al. | |
| 2009/0192584 A1 | 7/2009 | Gerdts et al. | |
| 2010/0137967 A1 | 6/2010 | Atlani et al. | |
| 2013/0018451 A1 | 1/2013 | Grabowski et al. | |

FOREIGN PATENT DOCUMENTS

WO 2011122444 10/2011

OTHER PUBLICATIONS

Search Report and Written Opinion for Application No. PCT/2013/035107, mailed on Jul. 26, 2013.

* cited by examiner

*Primary Examiner* — Anh Dang
(74) *Attorney, Agent, or Firm* — Seager, Tufte & Wickhem, LLP

(57) ABSTRACT

A handle for delivering a medical device comprises a housing having therein a wheel, a rack, and a catheter member. The wheel comprises a pinion gear that selectively engages gear teeth on the rack. The rack is selectively engaged and disengaged from the pinion gear in order to reduce the force necessary to manually pull the rack.

4 Claims, 12 Drawing Sheets

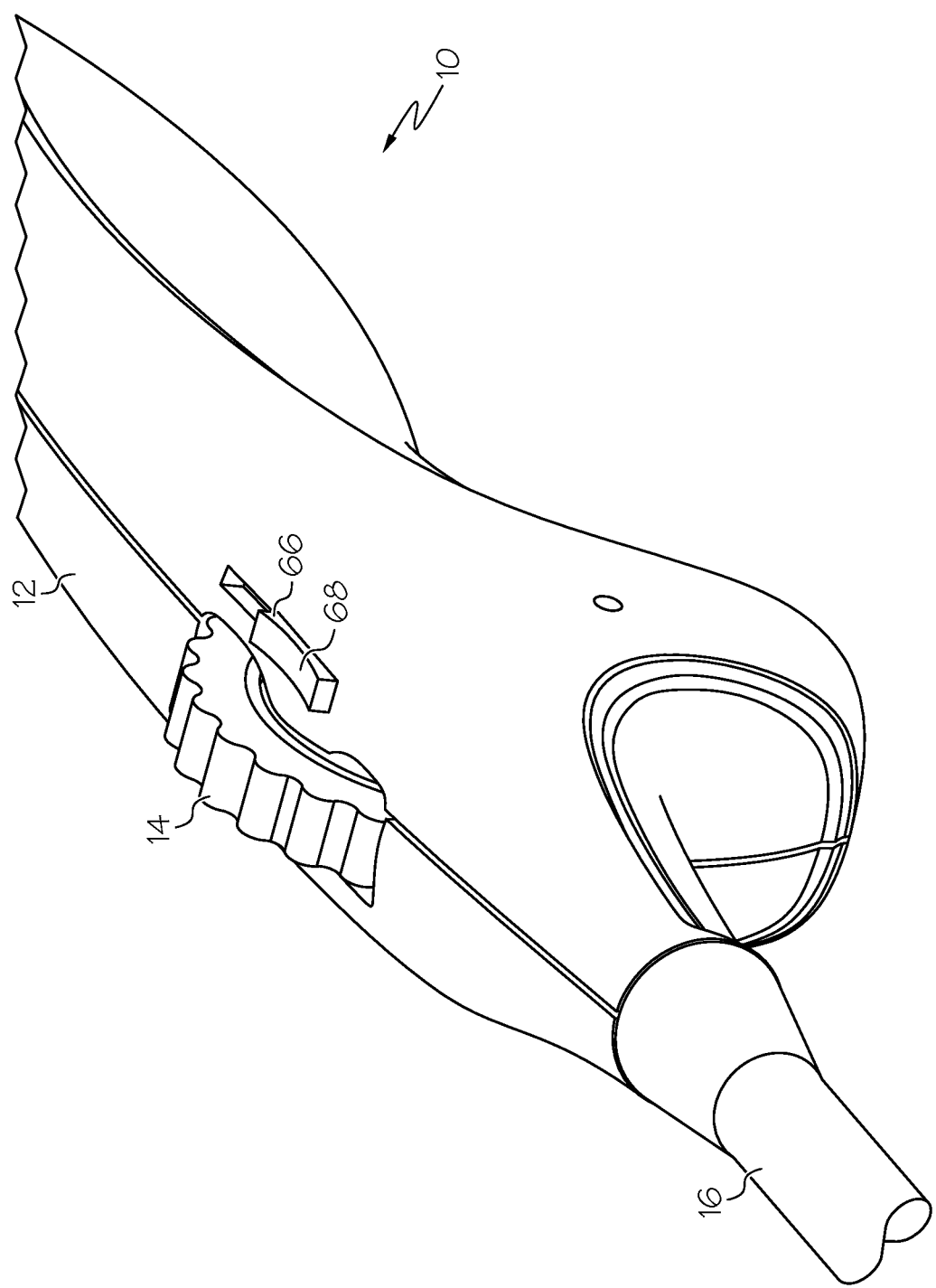

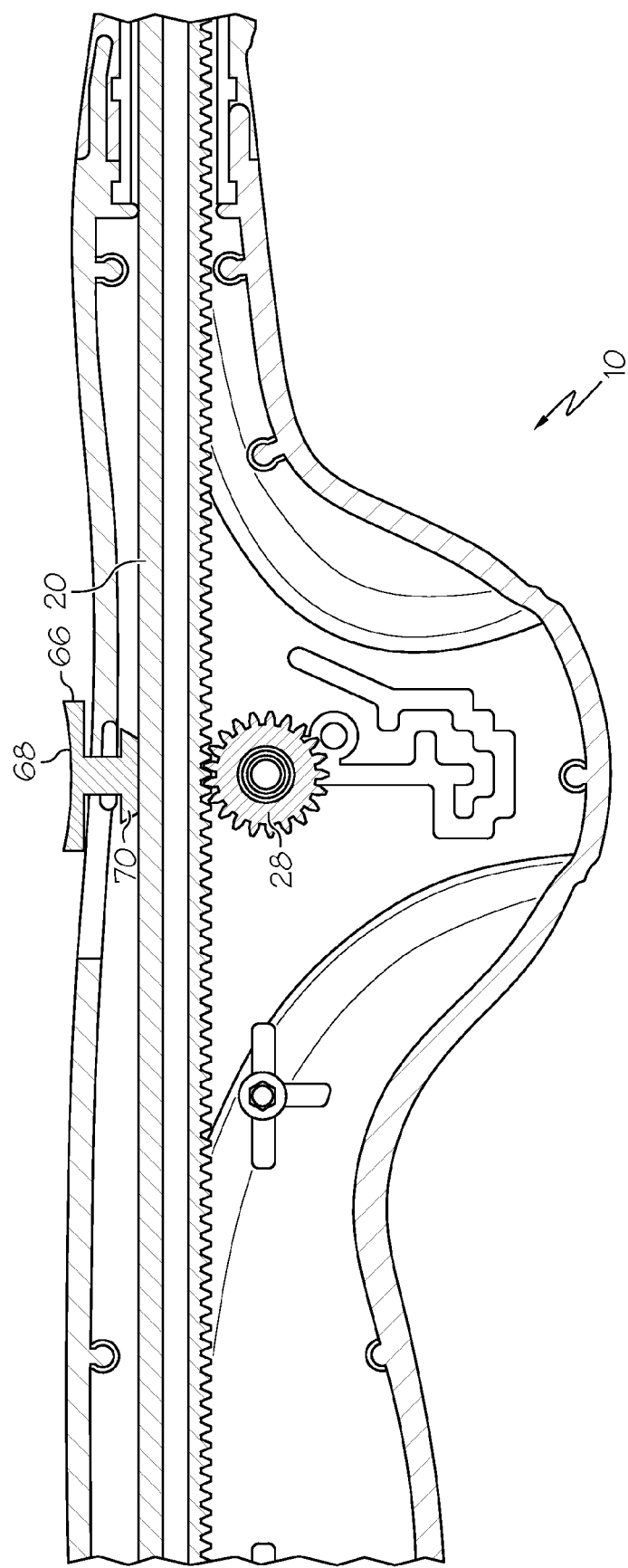

HANDLE FOR DELIVERING MEDICAL DEVICE

CROSS-REFERENCE TO RELATED APPLICATIONS

This Application claims the benefit of and priority to U.S. Provisional Application No. 61/620,172, filed Apr. 4, 2012, the entire contents of which are herein incorporated by reference.

STATEMENT REGARDING FEDERALLY SPONSORED RESEARCH

Not Applicable.

BACKGROUND OF THE INVENTION

Heretofore, various types of deployment mechanisms have been employed for implanting stents and other expansible medical devices. Additionally, various types of handle arrangements are known for use with self-expanding stents. One of the problems associated with delivery of relatively long length self-expanding stents is that deployment of these stents requires a relatively high amount of force to remove a sheath or other retainer. Higher forces associated with delivery, in turn, can interfere with the accuracy of stent placement.

Consequently, there remains a need for a delivery handle that can accurately place an expansible medical device within a body lumen and cope with increased forces.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In some embodiments, a stent deployment handle comprises a housing defining a cut-out. The housing has therein a wheel, a rack, and a catheter member. In some embodiments, the wheel has a pinion gear and the rack has teeth selectively engaging the pinion gear. In some embodiments, the catheter member extends along at least a portion of the rack. In some embodiments, a switch is affixed to the catheter member, and the switch protrudes through the cut-out. In some embodiments, the switch is rotatable, and rotation of the switch rotates the rack such that the teeth selectively engage and disengage the pinion gear.

In some embodiments, the rack has a channel and the catheter member is disposed within the channel.

In some embodiments, the wheel has a diameter between three and seven times the diameter of the pinion gear.

In some embodiments, the stent deployment handle further comprises a tubular sheath attached to the rack, and the catheter member extends at least partially within the tubular sheath.

In some embodiments, the rack is moveable axially with respect to the catheter member.

In some embodiments, the rack comprises a pull knob at the proximal end thereof.

In some embodiments, the rack has a channel and the channel extends through the pull knob.

In some embodiments, a stent deployment handle comprises a housing and a rack deflector. In some embodiments, the housing has therein a wheel and a rack. In some embodiments, the wheel has a pinion gear and the rack has teeth selectively engaging the pinion gear; in some embodiments the rack further has a channel extending along its length. In some embodiments, the housing defines an opening, and the rack deflector extends through the opening and into the channel. The rack deflector has a first position and a second position, in the first position the teeth being engaged with the pinion gear and in the second position the teeth being disengaged from the pinion gear.

In some embodiments, the rack deflector is slidable between the first and second positions.

In some embodiments, the deployment handle further comprises a pawl contacting the pinion gear.

In some embodiments, the pawl comprises a metallic spring.

BRIEF DESCRIPTION OF THE SEVERAL VIEWS OF THE DRAWING(S)

FIG. 6 shows a perspective view of an embodiment of the deployment handle.

FIGS. 6A and 6B show cross-sectional views of the deployment handle of FIG. 6.

DETAILED DESCRIPTION OF THE INVENTION

Figure 1:
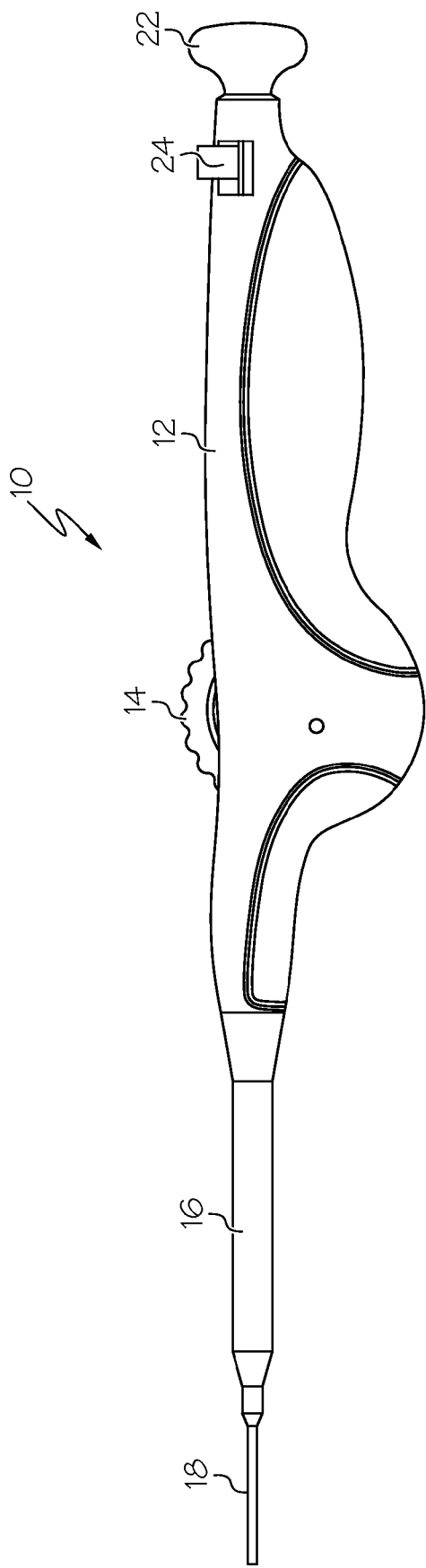
FIG. 1 shows a side view of an embodiment of a deployment handle.

While this invention may be embodied in many different forms, there are described in detail herein specific embodiments. This description is an exemplification of the principles of the invention and is not intended to limit it to the particular embodiments illustrated.

For the purposes of this disclosure, like reference numerals in the figures shall refer to like features unless otherwise indicated.

With reference to FIG. 1, an embodiment of a deployment handle 10 is shown therein. In some embodiments, the deployment handle 10 comprises a housing 12 and a wheel 14 disposed at least partially within the housing 12. In some embodiments, the deployment handle 10 further comprises a guide tube 16 at the end of the deployment handle 10. In some embodiments, the guide tube 16 has an outer tubular member 18 extending therefrom.

Figure 2:
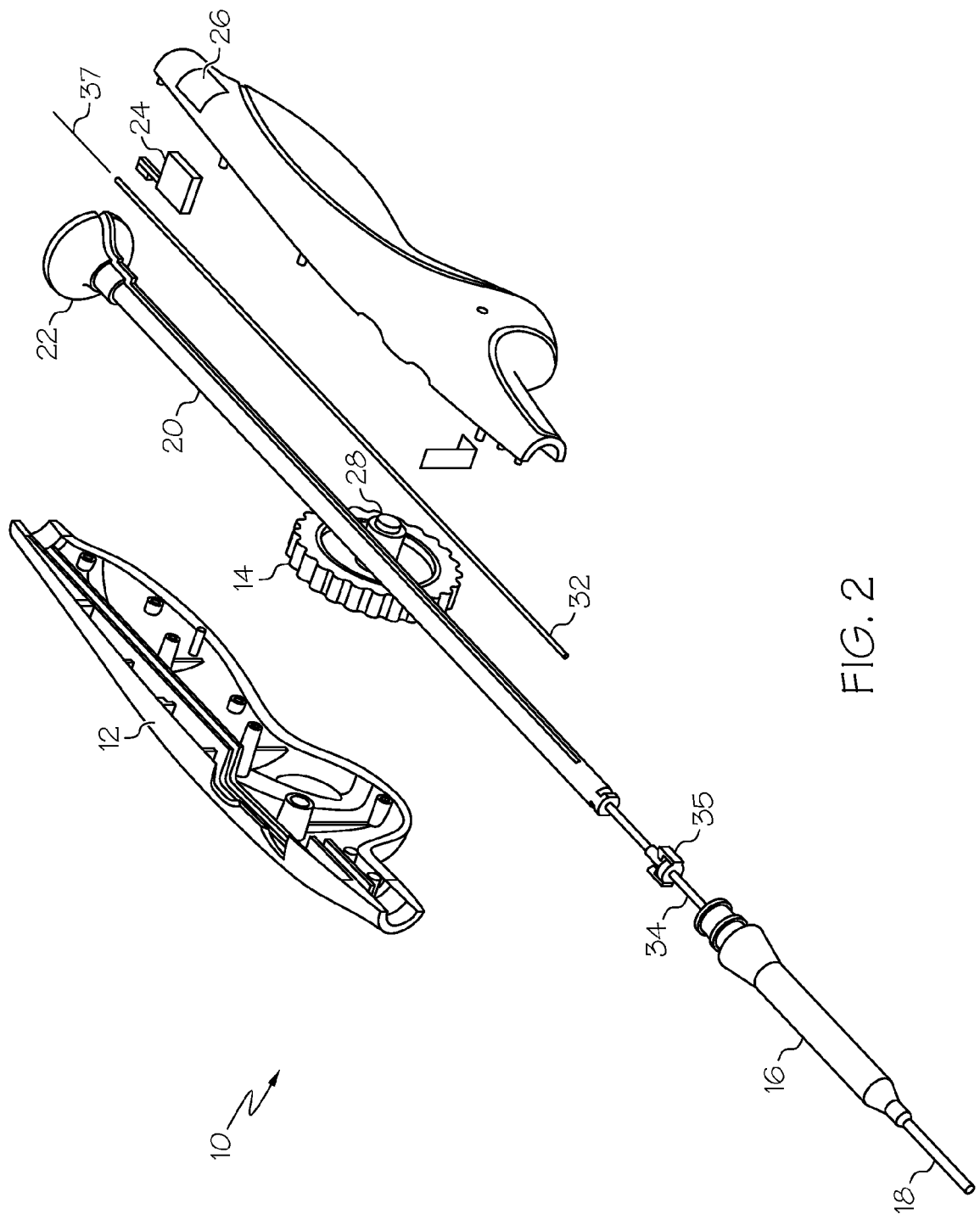
FIG. 2 shows an exploded view of the deployment handle of FIG. 1.

With regard to FIG. 2, an exploded view of the deployment handle 10 of FIG. 1 is shown therein. As illustrated in FIG. 2, in some embodiments, the housing 12 is formed from two-halves which are assembled together. Additionally, in some embodiments, the housing 12 has, therein, a rack 20. In some embodiments, the rack 20 comprises a pull knob 22 at its proximal end. As further illustrated, the wheel 14 comprises a pinion gear 28 that engages the teeth 30 (FIG. 3) of the rack 20.

Additionally, in some embodiments, a sheath 34 is attached to the rack 20 by way of retainer 35. An inner tubular member 32 is disposed within at least a portion of the sheath 34. The inner tubular member 32 is moveable with respect to the sheath 34.

In some embodiments, the inner tubular member 32 has a guidewire 37 that extends through the inner tubular member 32. As will be appreciated by the skilled artisan, the guidewire 37 serves to guide the inner tubular member 32 and sheath 34 through the body lumen during insertion.

In some embodiments, the inner tubular member 32 has a switch 24 attached thereto. Further, in some embodiments, the housing 12 has a cut-out 26 through which a portion of the switch 24 extends, upon assembly of the deployment handle 10.

Figure 3:
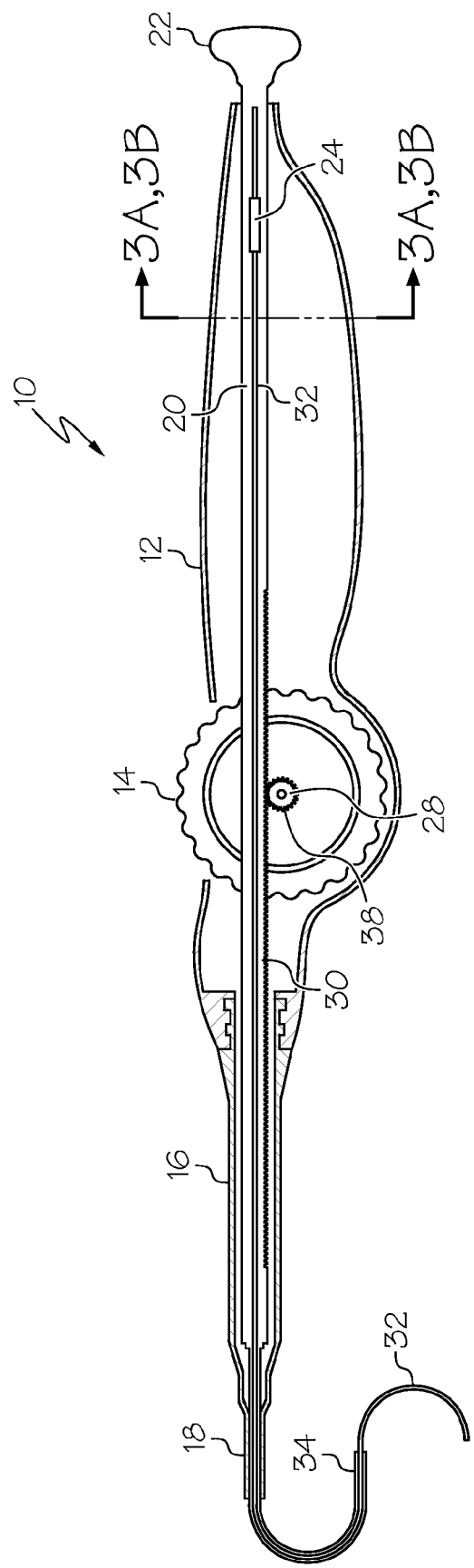
FIG. 3 shows a cutaway view of the deployment handle of FIG. 1.

Turning to FIG. 3, a partial cutaway view of the deployment handle 10 of FIG. 2 is shown therein. Such an arrangement is used, for example, in conjunction with a self-expanding stent. In this way, the sheath 34 is attached to the rack 20 and movable with respect to the housing 10. Moreover, the inner tubular member 32 is longitudinally fixed relative to the housing 10. Consequently, as the rack 20 is moved proximally, the sheath 34 is retracted relative to the catheter member 32, thereby permitting a stent or other medical device to expand.

In some embodiments, retraction of the sheath 34 is performed by rotation of the wheel 14, which results in rotation of the pinion gear 28. The teeth 30 of the rack 20 mesh with the teeth 38 of the pinion gear 28 such that rotation of the wheel 14 moves the rack 20. Additionally, in some embodiments, the wheel 14 has a diameter between three and seven times the diameter of the pinion gear 28, thereby providing a mechanical advantage. In some embodiments, the diameter of the wheel 14 is five times that of the pinion gear 28; the wheel 14 thusly provides a 5:1 mechanical advantage. Such a mechanical advantage is useful when deploying relatively long length stents, due to the force required for deployment. Further, the larger diameter of the wheel 14 in comparison to the pinion gear 28 yields a small amount of displacement in the rack 20 from a relatively large input in the wheel 14.

Figure 3B:
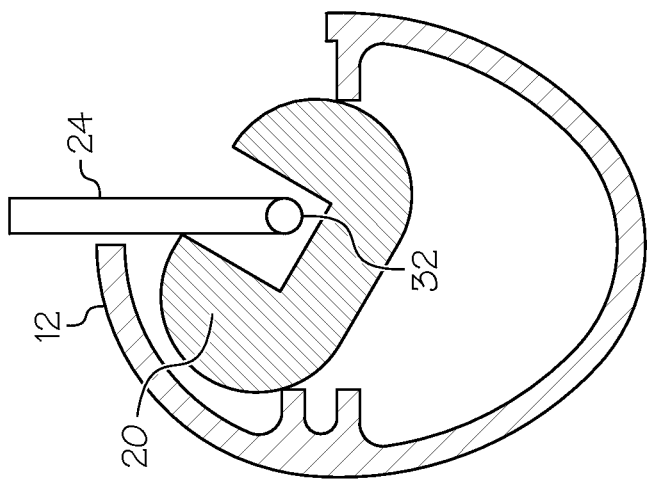
FIGS. 3A and 3B show cross-sectional views of the deployment handle of FIG. 1.

In some instances of deployment, after the rack 20 has been moved proximally sufficiently to ensure accurate placement of the stent, it is desirable to finish deployment of the stent by pulling directly on the pull knob 22. Pulling on the pull knob 22 while the rack 20 is engaged to the pinion gear 28 is difficult, however, due to the smaller diameter of the pinion gear 28 in comparison to the diameter of the wheel 14, and due to friction between the teeth 38 of the pinion gear 28 and the teeth 30 of the rack 20. Consequently, in some embodiments, the rack 20 is rotated, as shown via arrow 36 in FIG. 3A, to disengage the rack 20 from the pinion gear 28. As further shown in FIG. 3B, the rack 20 has been reoriented and the rack teeth 30 (FIG. 3) are no longer engaged with the teeth 38 of the pinion gear 28. Thereafter, the rack 20 can be pulled via pull knob 22 without spinning the wheel 14.

Figure 3A:
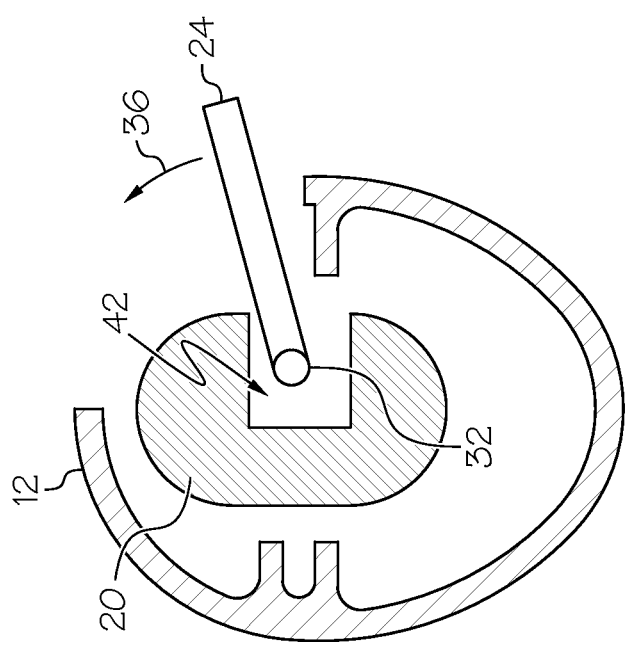

With further regard to FIG. 3A, in some embodiments, the rack 20 has a channel 42 in which the catheter member 32 resides. In some embodiments, the rack 20 can be used with a rapid exchange style catheter. In some embodiments, the channel 42 extends along at least a portion of the length of the rack 20. In some embodiments, the channel 42 extends through the pull knob 22, for example as shown in FIG. 2.

In order to rotate the rack 20 out of contact with the pinion gear 28, the switch 24 is rotated in the direction of arrow 36. The switch 24 contacts the rack 20 along channel 42 and, as the switch 24 is rotated, the rack 20 correspondingly moves out of contact with the pinion gear 28. The rack 20 can then be pulled via pull knob 22 without rotation of the wheel 14.

Figure 4:
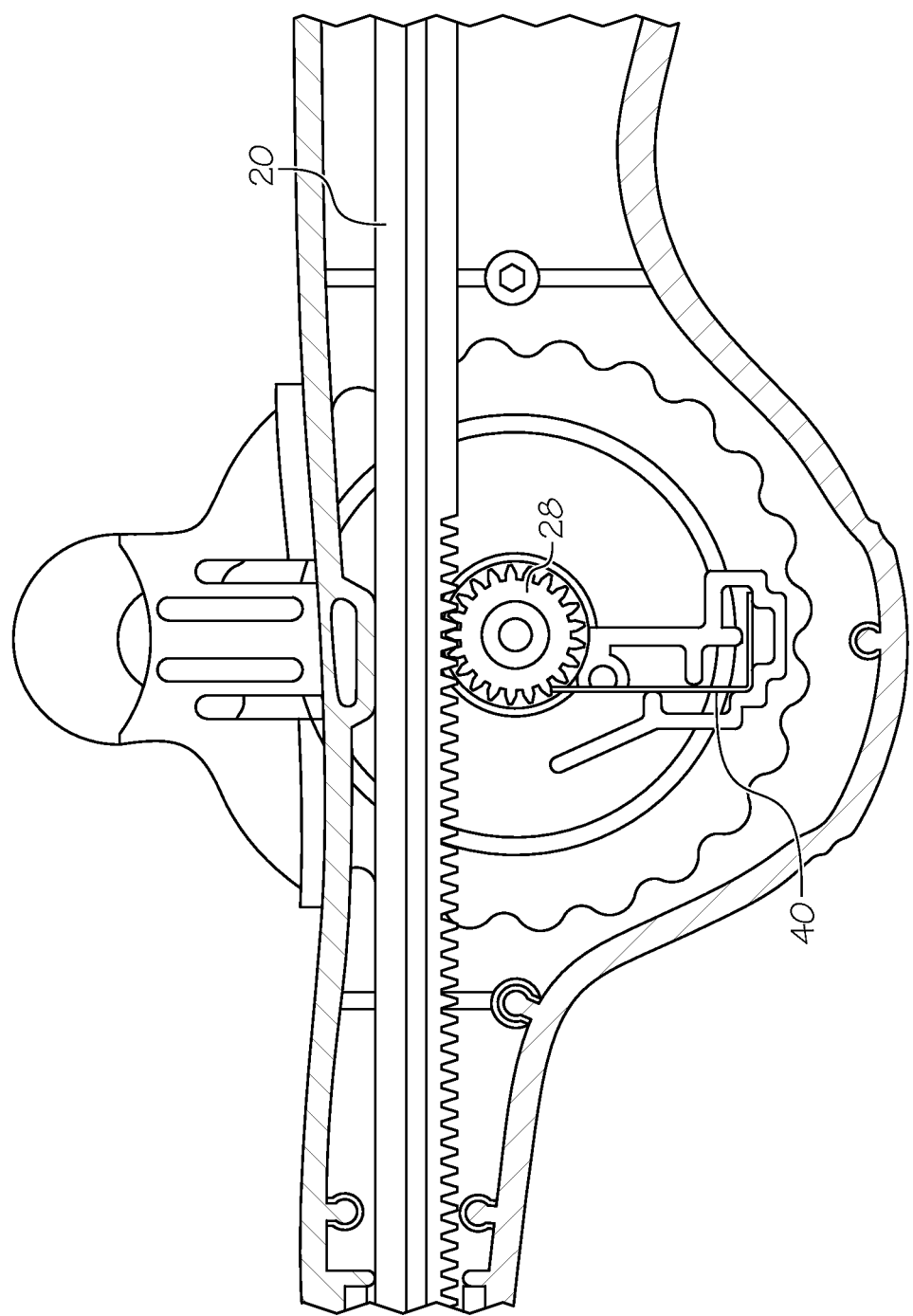
FIG. 4 shows a detailed cutaway view of the deployment handle of FIG. 1.

In some embodiments, the deployment handle 10 further comprises a stop member 40, for example as shown in FIG. 4. In some embodiments, the stop member 40 is positioned to permit rotation of the wheel 14 in only one direction, as will be evident to the skilled artisan. In some embodiments, the stop member 40 comprises a pawl that is engaged to the teeth 38 of the pinion gear 28. Other suitable stop members 40 are also permissible.

Figure 5:
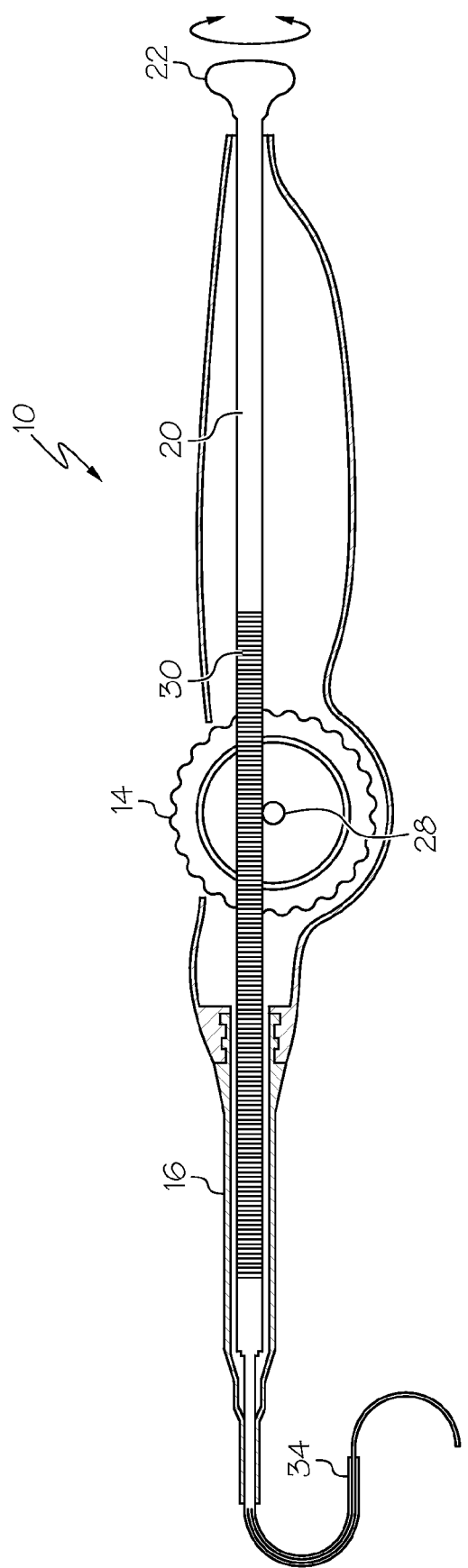
FIG. 5 shows a cutaway view of an embodiment of a deployment handle.

In some embodiments, for example as shown in FIG. 5, the rack 20 is disengaged from the pinion gear 28 by rotating the pull knob 22. In such an embodiment, the rack 20 is disengaged without the presence of a switch. More particularly, in such an embodiment, a stent (not shown) may be at least partially deployed by rotating the wheel 14 to move the rack 20 and retract the sheath 34. After the stent (not shown) is sufficiently deployed, the pull knob 22 is rotated to disengage the teeth 38 of the pinion gear 28 from the teeth 30 of the rack 20. Thereafter, the pull knob 22 is pulled proximally and the sheath 34 is more completely retracted.

Figure 6B:
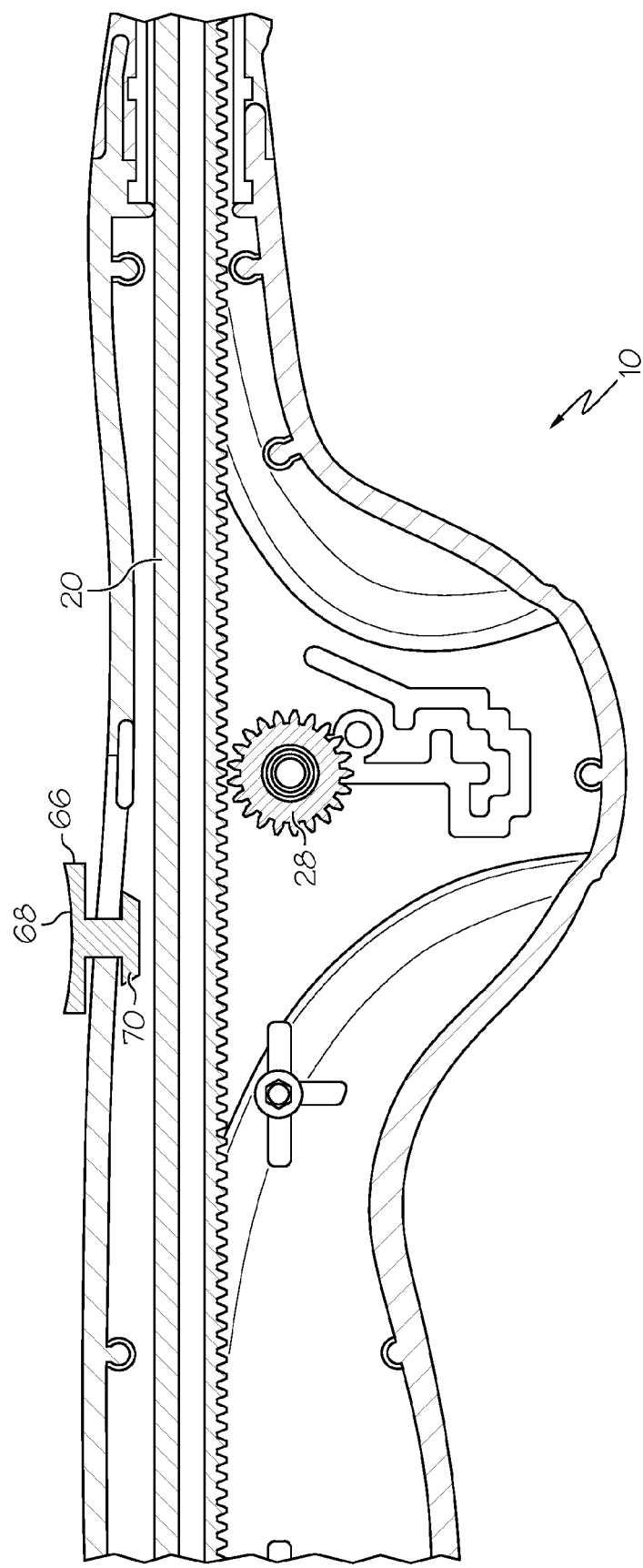

In some embodiments, for example as shown in FIG. 6, the deployment handle 10 comprises a slide member 66. As further shown in FIGS. 6A and 6B, the slide member 66 comprises a thumb contact portion 68 and a rack contact portion 70. In a first position, for example as shown in FIG. 6A, the slide member 66, and in particular the rack contact portion 70, is in contact with the rack 20. In this way, the slide member 66 presses on the rack 20 so the rack 20 maintains contact with the pinion gear 28.

Turning to FIG. 6B, when the slide member 66 is slid forward, it no longer presses the rack 20 against the pinion gear 28. Consequently, the rack 20 is able to disengage from the pinion gear 28 and the rack 20 can be "pulled" via pull knob 22 (not shown in FIGS. 6-6B) without turning the pinion gear 28.

Figure 7:
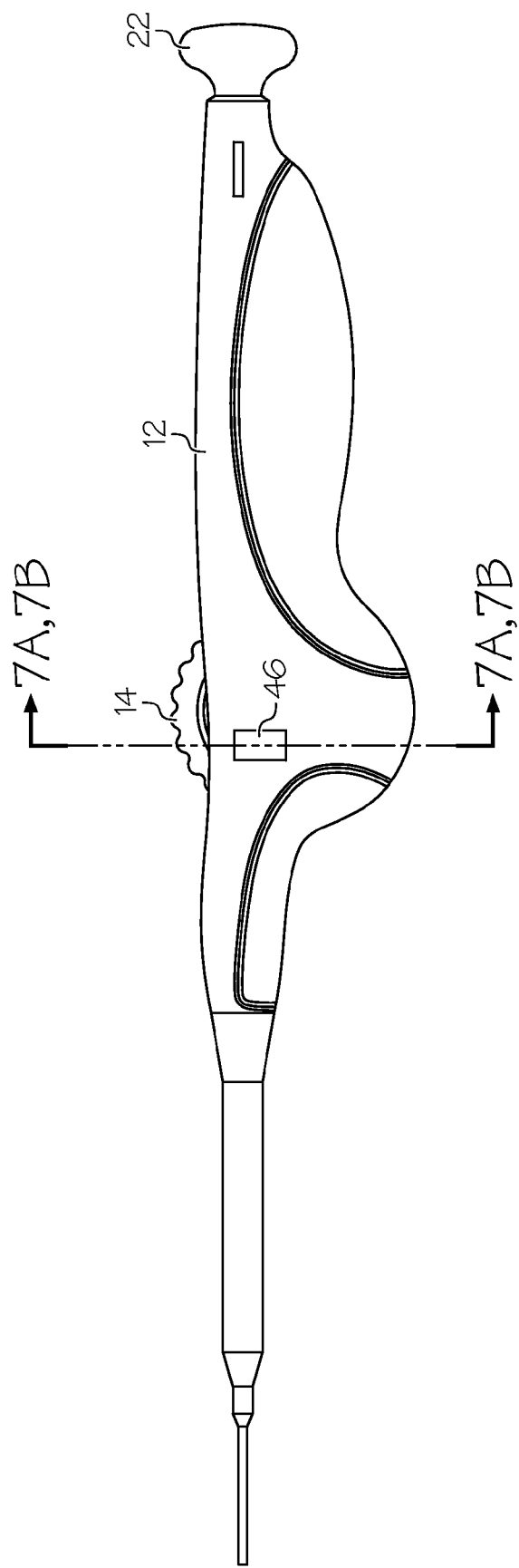
FIG. 7 shows a side view of an embodiment of a deployment handle.
Figure 7A:
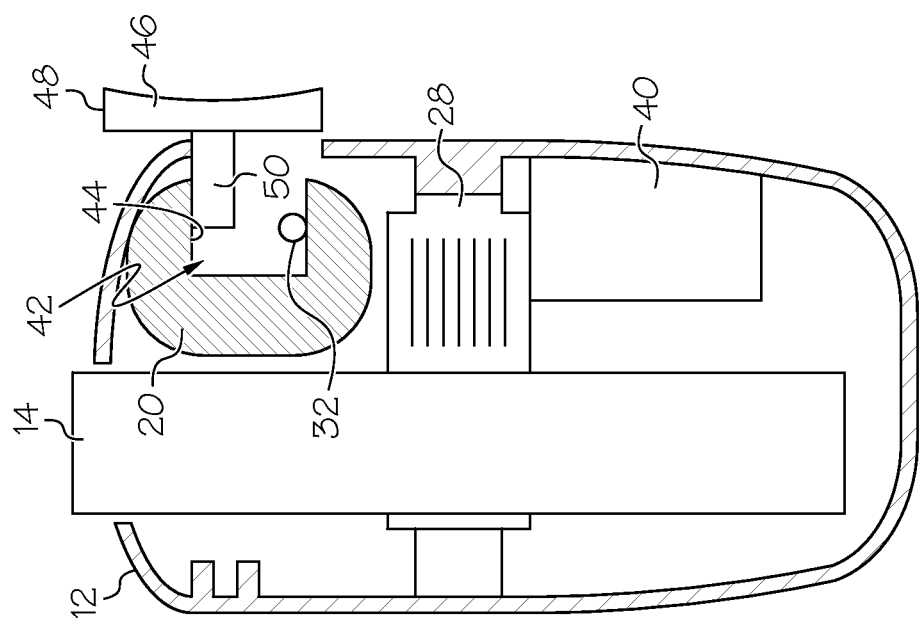
FIGS. 7A and 7B show cross-sectional views of the deployment handle of FIG. 7.
Figure 7B:
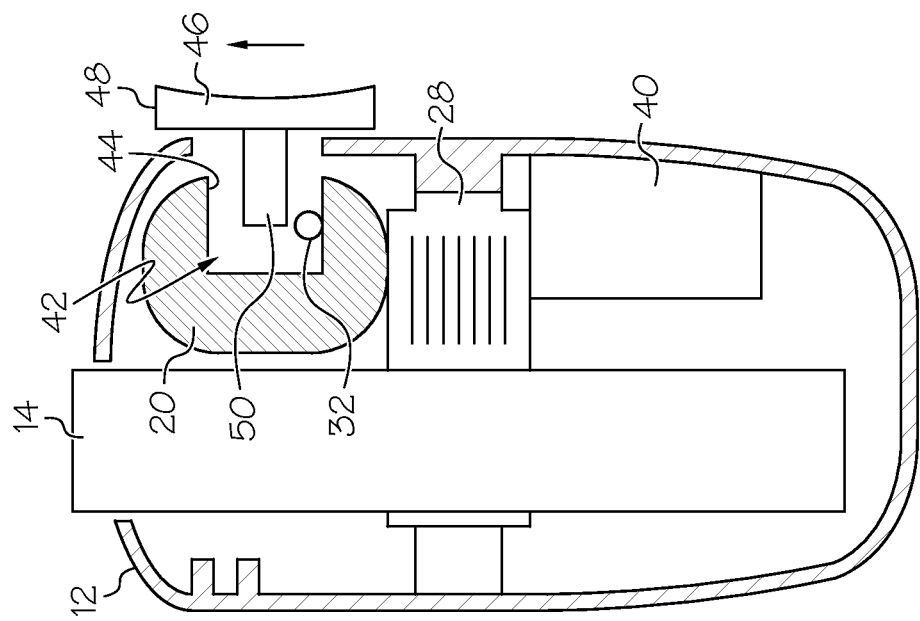

With regard to FIG. 7, in some embodiments, the deployment handle 10 comprises a rack deflector 46. As further shown in FIGS. 7A and 7B, in some embodiments the rack deflector 46 comprises an actuator portion 48 and a rack engaging portion 50. The actuator portion 48 can be actuated, for example, with the operator's thumb, thereby raising the rack 20 out of contact with the pinion gear 28, as shown in FIG. 7B. In this way, the rack 20 can be pulled via pull knob 22 without rotation of the wheel 14.

In some embodiments, the rack engaging portion 50 is disposed within the channel 42 of the rack 20. In some embodiments, the rack 20 is raised away from the pinion gear 28 as the rack engaging portion 50 engages the upper surface 44 of the channel 42.

Figure 8:
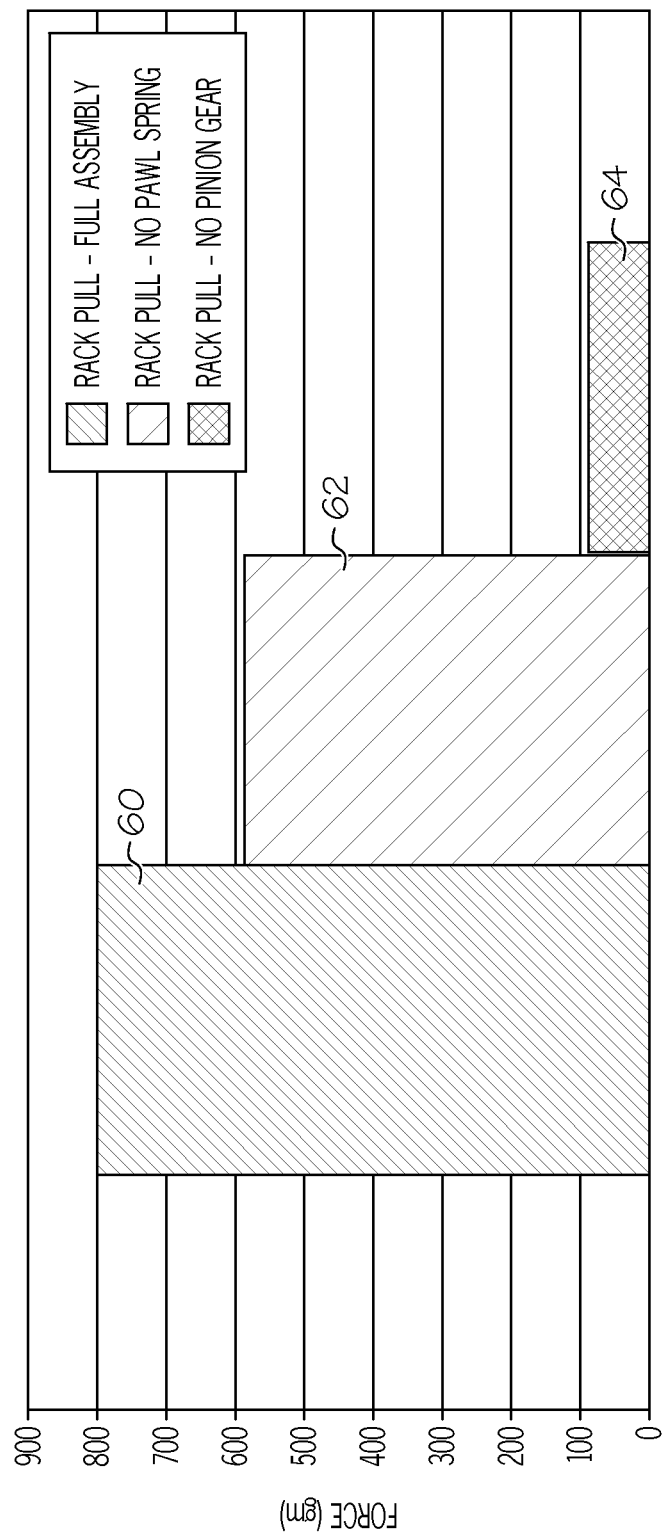
FIG. 8 shows a chart illustrating the force required to pull the rack in each of three scenarios.

Turning to FIG. 8, a chart depicting the peak force required to pull the rack 20 is shown in each of three scenarios. The first vertical bar 60 illustrates the amount of force required to pull the rack 20 when it is engaged to the pinion gear 28 and the pinion gear 28 is in contact with the stop member 40, in this case a pawl. The second vertical bar 62 illustrates the amount of force required to pull the rack 20 when it is engaged to the pinion gear 28 with the stop member 40 removed from the assembly. Finally, third vertical bar 64 illustrates the amount of force required to pull the rack 20 when it is disengaged from the pinion gear 28 altogether. In comparison to the first scenario (illustrated via first vertical bar 60), the third scenario (illustrated by the third vertical bar 64), requires approximately 11% as much force. Consequently, it is evident that disengagement of the rack from the wheel 14 is beneficial in reducing the amount of force required to pull the rack 20.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

What is claimed is:

1. A stent deployment handle comprising:
   a housing and a rack deflector, the housing having therein:
      a wheel, the wheel having a pinion gear including a plurality of teeth extending therefrom, the wheel having a diameter that is between three and seven times a diameter of the pinion gear; and
      a rack including a plurality of teeth extending therefrom, wherein the plurality of teeth on the rack extends between and contacts the plurality of teeth on the pinion gear and, wherein the rack includes a channel extending along its length, wherein the rack is capable of shifting between a first position where at least some of the plurality of teeth on the rack are in contact with at least some of the plurality of teeth on the pinion gear and a second position where the plurality of teeth on the rack are disengaged and free from contact with the plurality of teeth on the pinion gear;
   the housing defining an opening, and the rack deflector extending through the opening and into the channel, the rack deflector having a first position and a second position, in the first position at least some of the plurality of teeth on the rack being in contact with the pinion gear and in the second position the plurality of teeth on the rack being disengaged and free from the plurality of teeth on the pinion gear.

2. The stent deployment handle of claim 1, wherein the rack deflector is slidable between the first and second positions.

3. The stent deployment handle of claim 1 further comprising a pawl contacting the pinion gear.

4. The stent deployment handle of claim 3, wherein the pawl comprises a metallic spring.

* * * * *